(12) United States Patent
Harris et al.

(10) Patent No.: US 9,500,593 B2
(45) Date of Patent: Nov. 22, 2016

(54) LEAK DETECTION IN VACUUM BAGS

(71) Applicant: The Boeing Company, Chicago, IL (US)

(72) Inventors: John N. Harris, Seattle, WA (US); Finley Miller, Huntington Beach, CA (US); Michael R. Swift, Enfield, CT (US)

(73) Assignee: THE BOEING COMPANY, Chicago, IL (US)

( * ) Notice: Subject to any disclaimer, the term of this patent is extended or adjusted under 35 U.S.C. 154(b) by 189 days.

(21) Appl. No.: 14/217,478

(22) Filed: Mar. 18, 2014

(65) Prior Publication Data

US 2014/0199768 A1 Jul. 17, 2014

Related U.S. Application Data

(62) Division of application No. 12/764,202, filed on Apr. 21, 2010, now Pat. No. 8,707,766.

(51) Int. Cl.
*G01N 21/78* (2006.01)
*G01M 3/04* (2006.01)
*G01N 31/22* (2006.01)

(52) U.S. Cl.
CPC .............. *G01N 21/78* (2013.01); *G01M 3/04* (2013.01); *G01N 31/225* (2013.01); *G01M 3/042* (2013.01); *G01N 21/783* (2013.01)

(58) Field of Classification Search
CPC ..... G01N 21/78; G01N 31/225; G01M 3/04; G01M 3/042
USPC ............................... 73/49.3; 264/571; 436/3
See application file for complete search history.

(56) References Cited

U.S. PATENT DOCUMENTS

| | | | |
|---|---|---|---|
| 2,374,894 A | 5/1945 | Pioch et al. |
| 2,679,278 A | 5/1954 | Clark |
| 3,101,290 A | 8/1963 | Frederic et al. |
| 3,739,166 A | 6/1973 | Anderson |
| 3,983,282 A | 9/1976 | Seemann, III |
| 4,015,035 A | 3/1977 | Blad et al. |
| 4,016,022 A | 4/1977 | Browning et al. |
| 4,049,484 A | 9/1977 | Priest et al. |
| 4,120,632 A | 10/1978 | Stoeberl |
| 4,132,755 A | 1/1979 | Johnson |

(Continued)

FOREIGN PATENT DOCUMENTS

| | | |
|---|---|---|
| DE | 102004046520 A1 | 4/2005 |
| EP | 0230682 A2 | 8/1987 |

(Continued)

OTHER PUBLICATIONS

State Intellectual Property Office of PRC Notification of Second Office Action and English Translation, dated Jun. 24, 2015, regarding Application No. 201110038342.9, 7 pages.

(Continued)

*Primary Examiner* — Peter Macchiarolo
*Assistant Examiner* — Nathaniel Kolb
(74) *Attorney, Agent, or Firm* — Yee & Associates, P.C.

(57) ABSTRACT

A device indicates the location of an air leak in a vacuum bag used to process composite parts. The device includes a layer of material on the inner face of the bag that changes in appearance due to an oxidation-reduction reaction in areas of the layer exposed to oxygen caused by a leak in the bag.

9 Claims, 6 Drawing Sheets

(56) References Cited

U.S. PATENT DOCUMENTS

| | | | |
|---|---|---|---|
| 4,208,238 A | 6/1980 | August et al. |
| 4,238,539 A | 12/1980 | Yates et al. |
| 4,287,015 A | 9/1981 | Danner, Jr. |
| 4,476,797 A | 10/1984 | Ivanov et al. |
| 4,491,081 A | 1/1985 | Ivanov |
| 4,491,493 A | 1/1985 | Eaton |
| 4,496,412 A | 1/1985 | Ritter |
| 4,548,859 A | 10/1985 | Kline et al. |
| 4,554,036 A | 11/1985 | Newsom |
| 4,564,543 A | 1/1986 | Ritter |
| 4,588,626 A | 5/1986 | Cologna et al. |
| 4,622,091 A | 11/1986 | Letterman |
| 4,698,115 A | 10/1987 | Dodds |
| 4,741,943 A | 5/1988 | Hunt |
| 4,824,513 A | 4/1989 | Dodds |
| 4,875,962 A | 10/1989 | Breakspear |
| 4,902,215 A | 2/1990 | Seemann, III |
| 4,917,353 A | 4/1990 | Riley |
| 4,934,199 A | 6/1990 | Avila et al. |
| 4,942,013 A | 7/1990 | Palmer et al. |
| 4,945,488 A | 7/1990 | Carver et al. |
| 4,961,799 A | 10/1990 | Cologna et al. |
| 4,987,700 A | 1/1991 | Westerman et al. |
| 5,033,014 A | 7/1991 | Carver et al. |
| 5,034,254 A | 7/1991 | Cologna et al. |
| 5,052,906 A | 10/1991 | Seemann |
| 5,071,338 A | 12/1991 | Dublinski et al. |
| 5,087,193 A | 2/1992 | Herbert, Jr. |
| 5,116,216 A | 5/1992 | Cochran et al. |
| 5,123,985 A | 6/1992 | Evans et al. |
| 5,129,813 A | 7/1992 | Shepherd |
| 5,167,742 A | 12/1992 | Peters |
| 5,180,046 A | 1/1993 | Hutton et al. |
| 5,190,611 A | 3/1993 | Cologna et al. |
| 5,207,541 A | 5/1993 | Westerman et al. |
| 5,217,669 A | 6/1993 | Dublinski et al. |
| 5,290,386 A | 3/1994 | Trudeau |
| 5,316,462 A | 5/1994 | Seemann |
| 5,350,614 A | 9/1994 | Chase et al. |
| 5,359,887 A | 11/1994 | Schwab et al. |
| 5,364,584 A | 11/1994 | Imanara et al. |
| 5,427,518 A | 6/1995 | Morizot et al. |
| 5,427,725 A | 6/1995 | White et al. |
| 5,429,326 A | 7/1995 | Garesche et al. |
| 5,439,635 A | 8/1995 | Seemann |
| 5,441,692 A | 8/1995 | Taricco |
| 5,514,232 A | 5/1996 | Burns |
| 5,576,030 A | 11/1996 | Hooper |
| 5,601,852 A | 2/1997 | Seemann |
| 5,612,492 A | 3/1997 | Schwab et al. |
| 5,667,881 A | 9/1997 | Rasmussen et al. |
| 5,683,646 A | 11/1997 | Reiling, Jr. |
| 5,702,663 A | 12/1997 | Seemann |
| 5,721,034 A | 2/1998 | Seemann, III et al. |
| 5,759,325 A | 6/1998 | Davis |
| 5,780,721 A | 7/1998 | Levens |
| 5,820,894 A | 10/1998 | Kreutzer |
| 5,879,489 A | 3/1999 | Burns et al. |
| 5,882,756 A | 3/1999 | Alston et al. |
| 5,904,972 A | 5/1999 | Tunis, III et al. |
| 5,932,256 A | 8/1999 | Mandish |
| 5,939,013 A | 8/1999 | Han et al. |
| 5,954,898 A | 9/1999 | McKague et al. |
| 5,958,325 A | 9/1999 | Seemann, III et al. |
| 6,090,335 A | 7/2000 | McClure et al. |
| 6,093,572 A | 7/2000 | Stenholm et al. |
| 6,096,164 A | 8/2000 | Benson et al. |
| 6,206,067 B1 | 3/2001 | Kociemba et al. |
| 6,211,497 B1 | 4/2001 | Matsen et al. |
| 6,284,089 B1 | 9/2001 | Anderson et al. |
| 6,298,896 B1 | 10/2001 | Sherrill et al. |
| 6,299,819 B1 | 10/2001 | Han |
| 6,325,974 B1 | 12/2001 | Ahvenainen et al. |
| 6,355,203 B1 | 3/2002 | Charmes et al. |
| 6,391,246 B2 | 5/2002 | Shiraishi et al. |
| 6,391,436 B1 | 5/2002 | Xu et al. |
| 6,406,659 B1 | 6/2002 | Lang et al. |
| 6,408,517 B1 | 6/2002 | Lehmker et al. |
| 6,461,551 B1 | 10/2002 | Mandish |
| 6,510,977 B1 | 1/2003 | Hertz |
| 6,533,985 B1 | 3/2003 | Smith |
| 6,551,091 B1 | 4/2003 | Bryant et al. |
| 6,575,218 B1 | 6/2003 | Burns et al. |
| 6,579,418 B2 | 6/2003 | Lindsay et al. |
| 6,589,472 B1 | 7/2003 | Benson et al. |
| 6,638,466 B1 | 10/2003 | Abbott |
| 6,689,438 B2 | 2/2004 | Kennedy et al. |
| 6,692,681 B1 | 2/2004 | Lunde |
| 6,696,690 B2 | 2/2004 | Benne |
| 6,761,783 B2 | 7/2004 | Keller et al. |
| 6,797,390 B2 | 9/2004 | Asai et al. |
| 6,808,143 B2 | 10/2004 | Munk et al. |
| 6,830,079 B1 | 12/2004 | Ahrens et al. |
| 6,860,957 B2 | 3/2005 | Sana et al. |
| 6,919,039 B2 | 7/2005 | Lang et al. |
| 7,029,267 B2 | 4/2006 | Caron |
| 7,127,950 B2 | 10/2006 | Fonov et al. |
| 7,137,182 B2 | 11/2006 | Nelson |
| 7,141,191 B2 | 11/2006 | Engwall et al. |
| 7,186,367 B2 | 3/2007 | Hou et al. |
| 7,228,611 B2 | 6/2007 | Anderson et al. |
| 7,294,220 B2 | 11/2007 | Anderson |
| 7,306,450 B2 | 12/2007 | Hanson |
| 7,398,586 B2 | 7/2008 | Prichard et al. |
| 7,398,698 B2 | 7/2008 | Griess et al. |
| 7,413,694 B2 | 8/2008 | Waldrop, III et al. |
| 7,503,368 B2 | 3/2009 | Chapman et al. |
| 7,521,105 B2 | 4/2009 | Bech et al. |
| 7,527,759 B2 | 5/2009 | Lee et al. |
| 7,534,615 B2 | 5/2009 | Havens |
| 7,622,066 B2 | 11/2009 | Brustad et al. |
| 7,624,488 B2 | 12/2009 | Lum et al. |
| 7,628,879 B2 | 12/2009 | Ackerman |
| 7,655,168 B2 | 2/2010 | Jones et al. |
| 7,762,122 B2 | 7/2010 | Advani et al. |
| 7,849,729 B2 | 12/2010 | Miller et al. |
| 7,871,040 B2 | 1/2011 | Lee et al. |
| 7,963,038 B2 | 6/2011 | Schmitz |
| 7,964,049 B2 | 6/2011 | Kapur et al. |
| 8,003,034 B2 | 8/2011 | Oldani et al. |
| 8,114,673 B2 | 2/2012 | Mills et al. |
| 8,333,864 B2 | 12/2012 | Brennan et al. |
| 8,409,396 B2 | 4/2013 | Bech et al. |
| 8,438,909 B2 | 5/2013 | Miller et al. |
| 8,505,361 B2 | 8/2013 | Miller et al. |
| 8,613,301 B2 | 12/2013 | Brennan et al. |
| 8,707,766 B2 | 4/2014 | Harris et al. |
| 8,752,293 B2 | 6/2014 | Jones et al. |
| 2002/0060018 A1 | 5/2002 | Lindsay et al. |
| 2003/0082321 A1 | 5/2003 | Kennedy et al. |
| 2003/0175511 A1 | 9/2003 | Asai et al. |
| 2004/0026025 A1 | 2/2004 | Sana et al. |
| 2004/0031567 A1 | 2/2004 | Engelbart et al. |
| 2004/0258562 A1* | 12/2004 | Mills .................. G01J 1/429 422/400 |
| 2005/0086916 A1 | 4/2005 | Caron et al. |
| 2005/0102814 A1 | 5/2005 | Anderson et al. |
| 2005/0112772 A1* | 5/2005 | Farone .................. G01N 21/78 436/151 |
| 2005/0161154 A1 | 7/2005 | Anderson |
| 2005/0230055 A1 | 10/2005 | Sana et al. |
| 2005/0236735 A1 | 10/2005 | Oldani et al. |
| 2005/0253309 A1 | 11/2005 | Hou et al. |
| 2006/0108058 A1 | 5/2006 | Chapman et al. |
| 2006/0118235 A1 | 6/2006 | Lum et al. |
| 2006/0121613 A1 | 6/2006 | Havens et al. |
| 2006/0260751 A1 | 11/2006 | Lauder et al. |
| 2007/0029527 A1 | 2/2007 | Mills et al. |
| 2007/0107189 A1 | 5/2007 | Prichard et al. |
| 2007/0272582 A1 | 11/2007 | Lau |
| 2007/0289246 A1 | 12/2007 | Schmitz |
| 2008/0023015 A1 | 1/2008 | Arnold et al. |
| 2008/0111024 A1 | 5/2008 | Lee et al. |

(56) References Cited

U.S. PATENT DOCUMENTS

| | | | |
|---|---|---|---|
| 2008/0148817 A1* | 6/2008 | Miller | G01M 3/227 73/40 |
| 2008/0178996 A1 | 7/2008 | Tada et al. | |
| 2008/0308674 A1 | 12/2008 | Frantz et al. | |
| 2009/0120562 A1 | 5/2009 | Tsotsis et al. | |
| 2009/0145545 A1 | 6/2009 | Brennan et al. | |
| 2009/0148647 A1 | 6/2009 | Jones et al. | |
| 2009/0211698 A1 | 8/2009 | McCowin | |
| 2009/0223432 A1 | 9/2009 | Kodama et al. | |
| 2009/0273107 A1 | 11/2009 | Advani et al. | |
| 2009/0320292 A1 | 12/2009 | Brennan et al. | |
| 2010/0011580 A1 | 1/2010 | Brennan et al. | |
| 2010/0012260 A1 | 1/2010 | Brennan et al. | |
| 2010/0078126 A1 | 4/2010 | Brennan et al. | |
| 2010/0170326 A1 | 7/2010 | Miller et al. | |
| 2011/0079174 A1 | 4/2011 | Miller et al. | |
| 2011/0259086 A1 | 10/2011 | Harris et al. | |
| 2011/0259515 A1 | 10/2011 | Rotter et al. | |
| 2013/0011586 A1 | 1/2013 | Landry et al. | |
| 2013/0042978 A1 | 2/2013 | Brennan et al. | |
| 2013/0239875 A1 | 9/2013 | Miller et al. | |

FOREIGN PATENT DOCUMENTS

| | | |
|---|---|---|
| EP | 0271263 A2 | 6/1988 |
| EP | 0319449 A2 | 6/1989 |
| EP | 0348831 A2 | 1/1990 |
| EP | 0391641 A1 | 10/1990 |
| EP | 0391641 B1 | 8/1994 |
| EP | 0629497 A2 | 12/1994 |
| EP | 0816438 A2 | 1/1998 |
| EP | 1038656 A1 | 9/2000 |
| EP | 1780120 A2 | 5/2007 |
| EP | 1995044 A2 | 11/2008 |
| EP | 1995045 A2 | 11/2008 |
| EP | 2067611 A1 | 6/2009 |
| EP | 2383106 A1 | 11/2011 |
| EP | 2383559 A1 | 11/2011 |
| EP | 2444240 A1 | 4/2012 |
| GB | 2478848 A | 9/2011 |
| JP | 60252235 A | 12/1985 |
| JP | 62259059 A | 11/1987 |
| JP | H10219853 A | 8/1998 |
| JP | 2004309379 A | 11/2004 |
| KR | 19970058260 A1 | 11/1997 |
| WO | WO9322127 A1 | 11/1993 |
| WO | WO0176892 A1 | 10/2001 |
| WO | WO02099416 A1 | 12/2002 |
| WO | WO03021252 A1 | 3/2003 |
| WO | WO2004031321 A1 | 4/2004 |
| WO | 2004078461 A1 | 9/2004 |
| WO | WO2005056391 A2 | 6/2005 |
| WO | WO2005059500 A1 | 6/2005 |
| WO | WO2006110627 A1 | 10/2006 |
| WO | WO2006118692 A1 | 11/2006 |
| WO | WO2008054499 A2 | 5/2008 |
| WO | WO2008088435 A1 | 7/2008 |
| WO | WO2010025376 A1 | 3/2010 |

OTHER PUBLICATIONS

Canadian Intellectual Property Office Examination Search Report, dated May 20, 2015, regarding Application No. 2,735,435, 3 pages.
Extended European Search Report, dated Sep. 11, 2015, regarding Application No. EP15167436.3, 7 pages.
Notice of Allowance, dated Sep. 3, 2014, regarding U.S. Appl. No. 12/768,007, 8 pages.
Office Action, dated Apr. 1, 2013, regarding U.S. Appl. No. 12/764,202, 38 pages.
Final Office Action, dated Aug. 15, 2013, regarding U.S. Appl. No. 12/764,202, 16 pages.
Notice of Allowance, dated Dec. 6, 2013, regarding U.S. Appl. No. 12/764,202, 20 pages.
Office Action dated Nov. 14, 2011, regarding U.S. Appl. No. 12/768,007, 20 pages.
Final Office Action, dated May 3, 2012, regarding U.S. Appl. No. 12/768,007, 29 pages.
Office Action, dated May 22, 2014, regarding U.S. Appl. No. 12/768,007, 67 pages.
European Search Report dated Mar. 2, 2009 regarding Application No. EP08171011 (EP2067611), 2 pages.
European Search Report, dated Sep. 30, 2011, regarding Application No. EP11160843 (EP2383559), 7 pages.
European Search Report dated Sep. 15, 2011 regarding Application No. EP11160866 (EP2383106), 4 pages.
European Search Report dated Mar. 2, 2012 regarding Application No. EP12151305 (EP2444240), 2 pages.
UK Intellectual Property Office Search Report dated Jul. 15, 2011 regarding Application No. GB1104472.4 (GB2478848), 5 pages.
International Search Report dated May 29, 2008 regarding Application No. PCT/US2007/023455 (WO2008088435), 3 pages.
International Search Report dated Feb. 1, 2010 regarding Application No. PCT/US2009/055378 (WO2010025376), 3 pages.
Korean Intellectual Property Office Notice of Office Action dated Jun. 11, 2010, regarding Application No. 200847564, 9 pages.
Korean Intellectual Property Office Notice of Office Action dated Jun. 21, 2010, regarding Application No. 200847566, 14 pages.
Buckingham et al., "Automating the manufacture of composite broadgoods," Composites Part A, vol. 27A, No. 3, Mar. 1996, pp. 191-200.
Campbell (Ed.), "Ply Collation: A Major Cost Driver," In: Manufacturing Processes for Advanced Composites, Elsevier Advanced Technology, Oxford, UK, pp. 131-173, 2004.
El Amin, "Nano ink indicates safety breach in food packaging," dated Nov. 14, 2006, 2 pages. Retrieved from http://www.foodproductiondaily.com/Quality-Safety/Nano-ink-indicates-safety-breach-in-food-packaging.
Jayaweera et al., "Adaptive robotic assembly of compliant aerostructure components," Robotics and Computer-Integrated Manufacturing, vol. 23, No. 2, Jan. 2007, pp. 180-194.
Lee et al., "Novel UV-Activated Colorimetric Oxygen Indicator," Chemistry of Materials, vol. 17, No. 10, May 2005, pp. 2744-2751.
Material Safety Data Sheet for Potassium indigotetrasulfonate, Sigma-Aldric Corporation, Dec. 13, 2012, 6 pages.
Mills et al., "UV-Activated Luminescence/Colourimetric O2 Indicator," International Journal of Photoenergy, vol. 2008, 2008, 6 pages.
Setnescu et al., "Polymer Films Doped with Colorants as Oxygen Sensitive Materials," Journal of Optoelectrics and Advanced Materials, vol. 8, No. 2, Apr. 2006, pp. 682-686.
Sieberg et al., "An advanced FRP manufacturing technique asserts itself: Practical experience with the vacuum injection process," Studiedag Vakuuminjecteren, XP002169062, Oct. 27, 1998, pp. 13-19. (German-language article, English translation attached).
Office Action dated Apr. 13, 2011 regarding U.S. Appl. No. 11/751,928, 19 pages.
Final Office Action dated Jun. 23, 2011 regarding U.S. Appl. No. 11/751,928, 11 pages.
Office Action dated Jan. 19, 2012 regarding U.S. Appl. No. 11/751,928, 13 pages.
Final Office Action, dated Jun. 20, 2012, regarding U.S. Appl. No. 11/751,928, 20 pages.
Office Action dated Mar. 10, 2010 regarding U.S. Appl. No. 11/829,900, 10 pages.
Notice of Allowance dated Jul. 30, 2010 regarding U.S. Appl. No. 11/829,900, 8 pages.
Notice of Allowance, dated Sep. 21, 2012, regarding U.S. Appl. No. 12/725,380, 19 pages.
Office Action dated Feb. 21, 2012 regarding U.S. Appl. No. 12/906,489, 15 pages.
Notice of Allowance, dated Jun. 13, 2012, regarding U.S. Appl. No. 12/906,489, 9 pages.
Notice of Allowance, dated Sep. 14, 2012, regarding U.S. Appl. No. 12/906,489, 34 pages.
Office Action dated Jun. 2, 2010 regarding U.S. Appl. No. 11/751,931, 15 pages.

(56) References Cited

OTHER PUBLICATIONS

Final Office Action dated Aug. 11, 2010, regarding U.S. Appl. No. 11/751,931, 29 pages.
Office Action dated May 20, 2011, regarding U.S. Appl. No. 11/751,931, 31 pages.
Final Office Action dated Sep. 28, 2011, regarding U.S. Appl. No. 11/751,931, 24 pages.
Notice of Allowance, dated May 10, 2013, regarding U.S. Appl. No. 11/751,931, 49 pages.
Office Action dated Oct. 26, 2010, regarding U.S. Appl. No. 11/952,222, 20 pages.
Final Office Action dated Apr. 15, 2011 regarding U.S. Appl. No. 11/952,222, 20 pages.
Office Action dated Oct. 3, 2011, regarding U.S. Appl. No. 11/952,222, 21 pages.
Final Office Action dated Apr. 30, 2012, regarding U.S. Appl. No. 11/952,222, 25 pages.
Office Action, dated Oct. 24, 2012, regarding U.S. Appl. No. 11/952,222, 39 pages.
Office Action, dated May 9, 2013, regarding U.S. Appl. No. 11/952,222, 27 pages.
Notice of Allowance dated Jul. 17, 2014, regarding U.S. Appl. No. 11/952,222, 15 pages.
Office Action dated May 17, 2010, regarding U.S. Appl. No. 12/200,882, 9 pages.
Final Office Action dated Oct. 26, 2010, regarding U.S. Appl. No. 12/200,882, 8 pages.
Office Action dated Mar. 21, 2013, regarding U.S. Appl. No. 12/200,882, 47 pages.
Final Office Action, dated Jul. 29, 2013, regarding U.S. Appl. No. 12/200,882, 10 pages.
Office Action dated Jul. 27, 2010, regarding U.S. Appl. No. 12/242,477, 13 pages.
Final Office Action dated Dec. 2, 2010, regarding U.S. Appl. No. 12/242,477, 15 pages.
Notice of Allowance, dated Jul. 5, 2012, regarding U.S. Appl. No. 12/242,477, 9 pages.
Office Action, dated Mar. 26, 2013, regarding U.S. Appl. No. 13/657,137, 41 pages.
Office Action, dated Apr. 26, 2012, regarding U.S. Appl. No. 12/764,202, 13 pages.
Final Office Action, dated Nov. 16, 2012, regarding U.S. Appl. No. 12/764,202, 31 pages.
European Patent Office Communication, dated Feb. 19, 2015, regarding Application No. EP12151305.5, 5 pages.
Campbell, "Adhesive Bonding and Integrally Cocured Structure," In: Manufacturing Processes for Advanced Composites, Elsevier Advanced Technology, Oxford, UK, Jan. 2004, pp. 242-245.
Notice of Allowance, dated Jan. 26, 2015, regarding U.S. Appl. No. 13/892,916, 64 pages.
European Examination Report, dated Feb. 17, 2016, regarding Application No. 11160843.6, 8 pages.
Office Action, dated Sep. 8, 2016, regarding U.S. Appl. No. 11/751,928, 36 pages.

* cited by examiner

LEAK DETECTION IN VACUUM BAGS

CROSS REFERENCE TO RELATED APPLICATIONS

This application is a divisional of application Ser. No. 12/764,202, filed Apr. 21, 2010, which is incorporated by reference herein in its entirety. This application is related to co-pending U.S. patent application Ser. No. 11/829,900 filed Jul. 28, 2007, which is incorporated by reference herein in its entirety.

TECHNICAL FIELD

This disclosure generally relates to techniques and equipment for detecting leaks in vacuum bags used in manufacturing processes, such as the curing of composite layups, and deals more particularly with a method and device that allows leak detection through visual observation.

BACKGROUND

Flexible vacuum bags are often used to compact and consolidate composite part layups during curing. These bags comprise an oxygen impermeable film such as nylon which sometimes develops leaks during the curing cycle. Bag leaks are difficult to detect and, if not quickly repaired, may result in parts that do not exhibit the desired mechanical properties.

A variety of techniques and equipment have been devised in the past to detect leaks in vacuum bags, but each may have disadvantages. For example, known leak detection techniques may require specialized equipment and/or operators, may be time consuming, may be less than completely reliable and/or may be impractical to use on relatively large parts.

One known technique for detecting bag leaks is performed by moving an ultrasonic listening device over the surface of a part. Leaking air may often cause a high pitch noise that can be detected by the listening device in order to identify the location of the leak. Another known leak detection technique uses helium leak detection equipment comprising a helium source and a helium detector. The helium source is moved slowly over the surface of the bag, while the helium detector is used to sense helium traveling from the source through the bag leak, thereby marking the location of the leak.

In the food industry, colorimetrc dyes have been used to detect air leaks in food packages in order to provide an indication that the packaged foods may be subject to spoilage. These colorimetric dyes are in the form of ink that is applied inside the food packaging, and which change color on exposure to oxygen, thereby providing a visual indication that the package contains a leak.

Accordingly, there is a need for a method and device for detecting leaks in vacuum bags used to process composite parts such as composite layups that avoids the need for specialized detection equipment and which provides a rapid visual indication of the location of bag leaks.

SUMMARY

The disclosed embodiments provide a method and apparatus for detecting leaks in flexible film bags used to process parts in industrial applications such as vacuum bag processing employed to compact and consolidate composite layups during curing, or to bond parts together. The method may also be used to detect leaks in substrates such as tools and other parts. The method relies on a color change in the bag that can be readily detected with the naked eye and therefore does not require detection equipment. A colorimetric material in the form of an ink or dye is applied to the inner face of the vacuum bag film. The ink exhibits a substantially homogeneous color prior to being activated. After the part is placed on a cure tool and covered with the vacuum bag, the bag is sealed to the tool. A vacuum is then drawn within the bag, causing the air pressure within the bag to drop, which then allows the atmospheric pressure to push the bag down onto the layup and compact the layup. The colorimetric material is activated by directing UV (ultraviolet) light through the transparent bag onto the ink. The incident UV light activates the ink, changing its color and rendering it reactive to oxygen. Following activation, the material exhibits localized changes in color when exposed to oxygen due to a leak.

According to one disclosed embodiment, a device is provided for indicating the location of an air leak in a vacuum bag used to compact composite parts. The device comprises a layer of material on the inner face of the bag that changes appearance due to an oxidation-reduction reaction in areas of the layer exposed to oxygen caused by a leak in the bag. The layer of material may comprise a colorimetric ink including an oxygen permeable binder having semiconductor nanoparticles dispersed therein. The material may further include an electron-donor material and a reduction-oxidation indicator material.

According to another embodiment, apparatus is provided for compacting a composite part, comprising a tool adapted to have the composite part placed thereon and a substantially transparent, gas impermeable film forming a bag adapted to be placed over the part and sealed to the tool. The apparatus further includes a selectively activatable, colorimetric ink on the inner face of the film for providing a visual indication of the location of any air leaks in the film. The apparatus also includes a vacuum source for drawing a vacuum within the bag, and a radiation source for directing radiation through the film onto the colorimetric ink for activating the ink after the vacuum has been drawn in the bag. The radiation source emits radiation generally within the ultraviolet band of wavelengths.

According to a further embodiment, a method is provided of detecting leaks in a transparent vacuum bag used to process parts. The method comprises applying a layer of material on the inner face of the bag that changes appearance in the area of an air leak in the bag, and visually observing changes in the appearance of the layer of material viewed through the bag. The method may further comprise activating the layer of material to become reactive to oxygen in the air entering the bag through the leak.

According to one disclosed embodiment, a method is provided of detecting leaks in a substrate. The method comprises applying a layer of material to an interior face of a substantially transparent bag and sealing the bag over the substrate. The material is activatable to an oxygen reactive state in which the color of the material changes in response to the exposure of the material to oxygen. The method further comprises generating a vacuum within the bag and activating the layer of material to its oxygen reactive state, following which leaks in the substrate may be detected by visually observing localized changes in the color of the material. The layer of material may be activated by subjecting the layer to UV light for a predetermined length of time.

According to another embodiment, a method is provided of processing a part, comprising providing a material that may be activated from a first state in which the material exhibits a first color, to a second state in which the material exhibits a second color that reverts substantially to a color when exposed to oxygen. The method further includes applying a layer of the material in its first state on an inner face of the oxygen impermeable film and placing the film over the part with the inner face of the film facing the part. The method also includes sealing the film around the part to form a vacuum chamber and drawing a vacuum within the chamber, following which the material may be activated from the first state to the second state. Air leaks in the film may be detected by visually observing a localized change in color in the layer of material. Activating the material is performed after the vacuum has been drawn. The activation of the material may be performed by directing UV light through the film onto the layer of material.

The disclosed embodiments provide a method and apparatus for detecting leaks in vacuum bags which is relatively quick, reliable and is not highly dependent upon sophisticated equipment to identify the location of leaks.

BRIEF DESCRIPTION OF THE ILLUSTRATIONS

DETAILED DESCRIPTION

Figure 1:
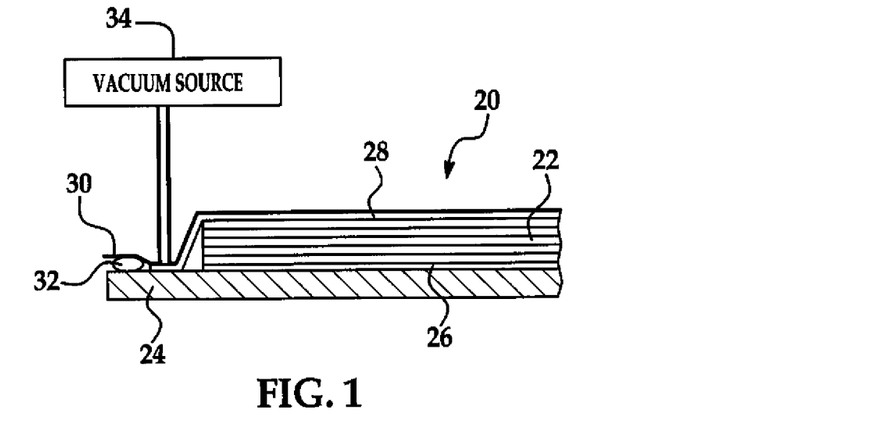
FIG. 1 is an illustration of a cross sectional view of a portion of a vacuum bag assembly used to compact a composite part layup.
Figure 2:
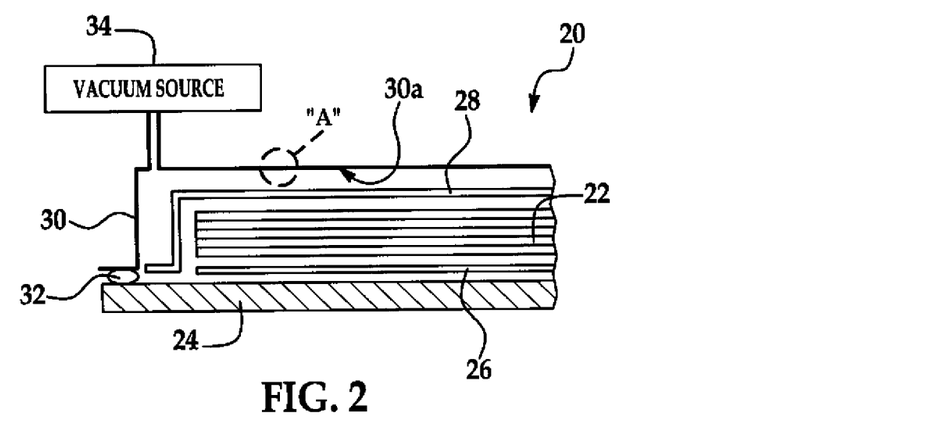
FIG. 2 is an illustration similar to FIG. 1, but exploded to better show the components of the assembly.

Referring first to FIGS. 1 and 2, a vacuum bag assembly 20 comprises a gas impermeable, substantially transparent vacuum bag 30 adapted to cover a part, such as a composite part layup 22 that is supported on a tool 24. The bag 30 is sealed around its periphery to the tool 24 by means of a peripheral seal 32 that extends around the perimeter of the part layup 22. The assembly 20 may further comprise any of various additional layers of material above or below the part layup 22, such as, without limitation, a release film 26 and a breather 28. The vacuum bag 30 may comprise a flexible film such as, for example and without limitation, nylon, that is coupled with a suitable vacuum source 34 for drawing a vacuum within the bag 30. A vacuum is drawn within the bag 30, causing the air pressure within the bag 30 to drop, which then allows the atmospheric pressure to push the bag 30 down onto the breather 28 and the layup 22. The atmospheric pressure pushing the bag 30 down applies compaction pressure to the layup 22 which assists in consolidating and compacting the layup 22 during the curing process. Although not specifically shown in FIGS. 1 and 2, one or more leaks may occur in the bag 30 which desirably should be detected as early as possible during the curing and/or compaction process, so that the bag 30 can be repaired or replaced before the part layup 22 is fully cured and/or compacted. In accordance with the disclosed embodiments, such leaks may be detected by visual observation with the naked eye, without the aid of equipment.

Figure 3:
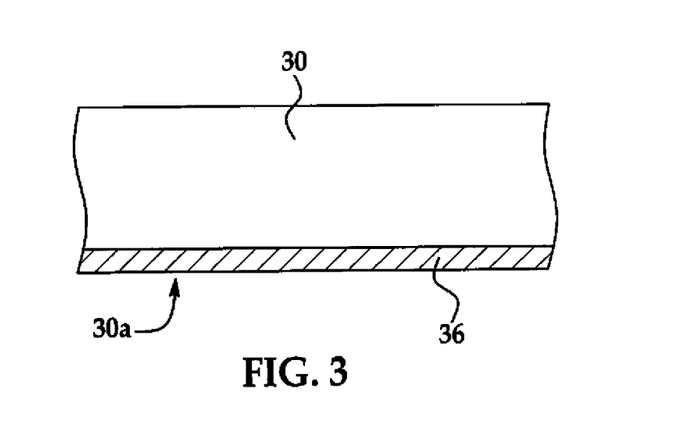
FIG. 3 is an illustration of the area designated as "A" in FIG. 2, and showing a layer of colorimetric ink having been applied to the inner face of the bag.

Referring now to FIG. 3, a layer of leak detection material 36, sometimes also referred to herein as a layer of colorimetric material, colorimetric ink or a colorimetric dye, is disposed between the inner face 30a of the bag 30, and the part layup 22. In the embodiment illustrated in FIG. 3, the layer of colorimetric material 36 is adhered to the inner face 30a of the bag 30, however in other embodiments, the colorimetric material 36 may be coextruded with the film from which the bag 30 is made so that it forms an integral part of the bag 30. In still other embodiments, the colorimetric material 36 may be applied to or integrated into an extruded film (not shown) that is separate from the bag 30.

The colorimetric material 36 comprises a mixture of an oxygen permeable polymer which functions as a binder, a dispersion of photoactive semiconductor nanoparticles held in the binder, a material that functions as an electron donor, and a material that acts as a reduction-oxidation (hereinafter "redox") indicator. The polymer binder may comprise, for example and without limitation, hydroxyethyl cellulose (HEC), and the semiconductor nanoparticles may comprise, for example and without limitation, a photoactive metal oxide such as $TiO_2$ (titanium dioxide). The electron donor material may comprise, for example and without limitation, glycerol, ascorbic acid or hydrazine and the redox indicator (reducing agent) may comprise without limitation, indigo-tetrasulfonate (ITS), methylene blue or dimethylmethylene blue.

Photoactive metal oxides are incorporated into the colorimetric material 36 in order to provide electron transport for the oxidation of the ITS. In its oxidized form, ITS is substantially colorless. The metal oxides suitable for the present application may exhibit arrangement of energy levels in the form of a band gap. The band gap is the difference in energy between the valance band where most of the electrons reside, and the conduction band which is a band of partially or completely unoccupied energy levels. In order for band gap materials to be photoactive, the energy gap between the valance and conduction bands of the material must equal the energy of a photon. $TiO_2$, for example, has a band gap energy of approximately 3.18 electron volts. This energy difference corresponds to a photon of 387 nm. Therefore, illumination of $TiO_2$ with 387 nm light will populate the conduction band with electrons.

Another feature of band gap materials is that the orbitals of the outer electrons on individual atoms will overlap each other, resulting in a delocalization of electrons. As a result, the electrons will exhibit some mobility among those orbitals that they partially occupied. The mobility or conductivity of electrons in the metal oxide effects the oxidation of the ITS redox indicator. In addition to $TiO_2$, other metal oxides that have band gaps satisfying the requirements for UV light excitation from a valance band to the conduction band may be employed in the ink 36. These materials include, but may not be limited to silicon carbide (SiC), zinc sulfide (ZNS), gallium nitride (GaN) and tantalum oxide ($Ta_2O_5$).

In one typical application, the colorimetric material 36 comprises an ink that may be prepared by the following process. A 5% HEC solution (i.e. 5 grams of HEC per 100 grams of water) is prepared, to which 0.2 grams of glycerol are added. An admixture of 0.02 grams of P25 photoactive metal oxides are incorporated into the bag film to provide electron transport for the oxidation of the ITS. $TiO_2$ and 0.005 grams of ITS are added to the solution of HEC and glycerol. The mixture is sonicated for approximately 15 minutes or stirred using a high speed mixer with a rotor stator attachment.

The colorimetric ink formulation described immediately above may be applied to the inner face 30a of the vacuum bag 30 by any of several techniques including, but not limited to printing, spin-casting or spraying. Alternatively, the colorimetric material 36 may be incorporated into the film forming the vacuum bag 30 by coextruding the material 36 along with the vacuum bag film, as mentioned previously. Additional details of suitable colorimetric materials and techniques for their preparation are described in the following publications which are incorporated by reference herein in their entireties: Andrew Mills, C. Tommons, R. Bailey, M. Tedford and P. Crilly, "UV-Activated Luminescence/Colourimetric O1 Indicator", *International Journal of Photoenergy*, Volume 2008, pp 2-6; and S. K. Lee, M. Sheridan and A. Mills, "Novel UV-Activated Colorimetric Oxygen Indicator", *Chemistry of Materials*, volume 17, no. 10, pp 2744-2751, 2005.

When initially applied to the bag 30 as described above, the layer of colorimetric material 36 exhibits a visible color largely determined by the material selected as the redox indicator. In the illustrated example the redox indicator comprises ITS which is relatively dark blue in color. Other colors may be possible, depending upon the material selected as the redox indicator. As used herein, the term "color" is intended to include all of the colors within the visible spectrum, including black and white. The term "colorless" is intended to mean substantially without color or substantially transparent. As initially applied in the illustrated example, the colorimetric material 36 employing ITS as the redox indicator has a relatively dark blue color, which can be visually observed through the transparent vacuum bag 30.

Figure 4:
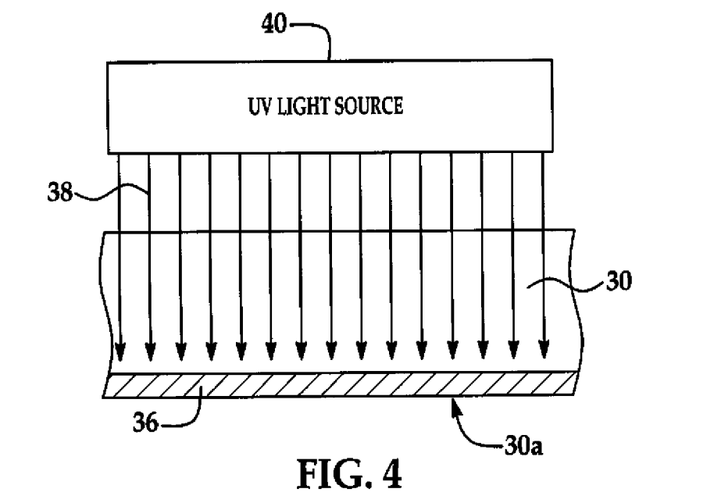
FIG. 4 is an illustration of a view similar to FIG. 3 but showing a UV light source radiating ultraviolet light through the bag onto the layer of colorimetric ink.

As will be discussed below in more detail, after the vacuum bag 30 is installed and evacuated of air, the colorimetric material 36 is "activated" by irradiating the material 36 with radiant energy of a suitable wavelength for a preselected period of time. The radiation may comprise, without limitation, UV (ultraviolet) light 38 generated by a UV light source 40. UV light comprises electromagnetic radiation having a wavelength generally in the range of approximately 10 nm to 400 nm, and energies from about 3 eV to 124 eV. In one practical example, use of UV light having a wavelength of approximately 390 nm yielded satisfactory results. The layer of colorimetric material 36 is irradiated with the UV light for a length of time sufficient for the material 36 to become substantially colorless, which in one example, requires approximately 30 seconds of applied UV light having a wavelength of 390 nm.

Figure 5:
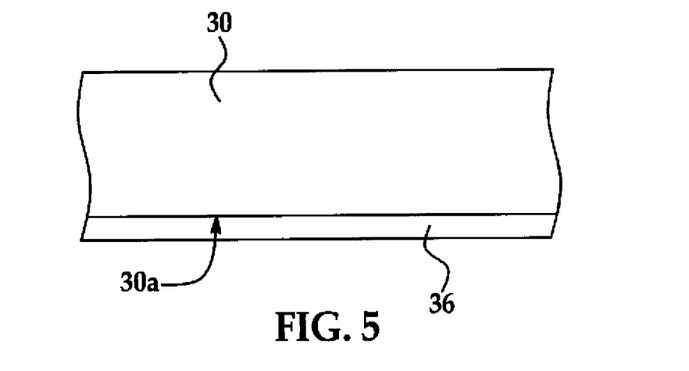
FIG. 5 is an illustration of a view similar to FIG. 3 but showing the layer of colorimetric ink having been activated to an oxygen sensitive state.

Prior to activation, the colorimetric material 36 exhibits the initial color of the redox indicator and is substantially non-reactive to oxygen. However, once activated by the UV light 38, the material 36 changes in appearance either to a different color or to a substantially colorless state in which it is reactive to oxygen. FIG. 5 illustrates the layer of colorimetric material 36 following activation by UV light 38, in which the material 36 is substantially colorless or transparent. Since the bag 30 remains evacuated and thus free of oxygen while the part layup 22 is curing, the colorimetric material 36 remains in its "activated" colored or colorless state unless and until it is exposed to oxygen as a result of a leak in the bag 30. As will be discussed below in connection with FIGS. 6-8, those areas of the material 36 that are exposed to oxygen as result of a leak exhibit a localized color change. This color change may comprise a change from a substantially colorless state, to a state in which the material 36 exhibits a color (which may or may not be the color of the material 36 prior to its activation) or from the color to which the material was activated to a different color. For example, after activation with UV light, an ITS that is initially blue but changes to a colorless state when activated by UV light, may change from colorless to green when exposed to oxygen. Regardless of the exact color to which the material changes after exposure to oxygen, the color change is readily visible to an operator without the aid of specialized equipment.

Figure 6:
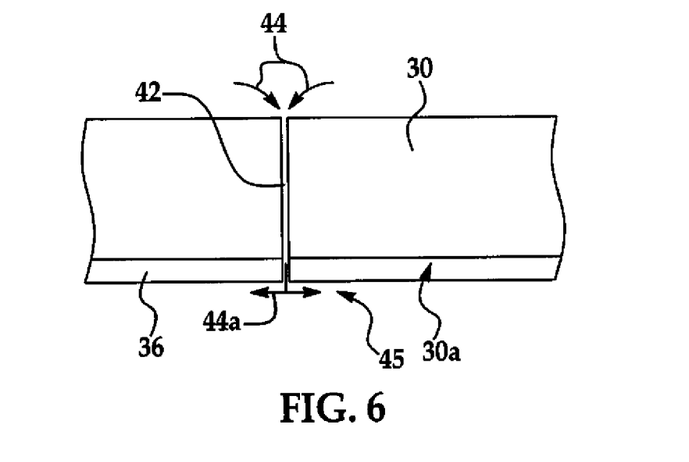
FIG. 6 is an illustration of a view similar to FIG. 5 but showing a leak in the bag.
Figure 7:
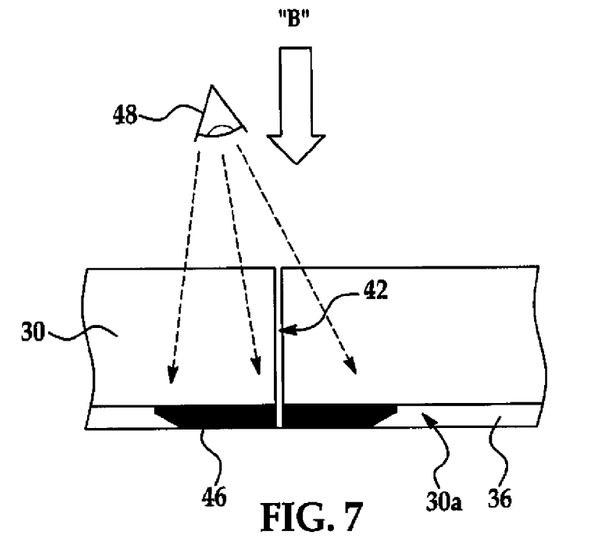
FIG. 7 is an illustration of a view similar to FIG. 6, but showing the layer of colorimetric ink exhibiting a visible color in the area of the leak.
Figure 8:
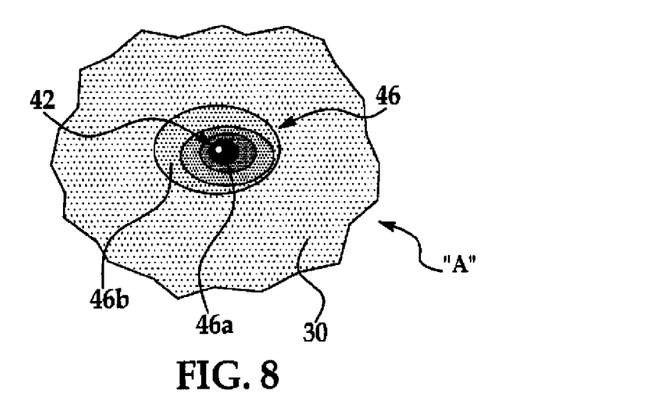
FIG. 8 is an illustration of the outer face of the bag taken in a direction designated as "B" in FIG. 7.

Referring now to FIGS. 6-8, a leak 42 in the bag 30 allows oxygen-containing air to flow through the leak 42, as indicated by the arrows 44. At the bottom 45 of the leak 42, near the inner face 30a of the bag, the incoming air increases the internal air pressure in the bag immediately surrounding the leak 42, allowing air to be redirected laterally as shown by the arrows 44a for a distance determined at least in part by the amount of pressure being applied by the bag 30 to the substrate 22.

As shown in FIG. 7, the portion 46 of the colorimetric material 36 surrounding the leak 42 reverts from a colorless state to a colored state upon exposure to the oxygen in the air drawn into the bag 30 through the leak 42. The "colorizing" or change in color of the material 36 in the area 46 surrounding the leak 42 is visible to the naked eye 48 through the transparent bag 30, thus allowing an operator to quickly see through visual observation the particular location of the leak 42. Depending upon the amount of pressure applied to the part layup 22 by the bag 30, the concentration of oxygen reaching the layer of colorimetric material 36 may be somewhat graduated with increasing lateral distance from the leak 42. Thus, as shown in FIG. 8, the intensity of the color appearing in the exposed area 46 of the material 36 may be graduated, with the areas 46a immediately surrounding the leak 42 being darker than those in the outlying areas 46b.

Figure 9:
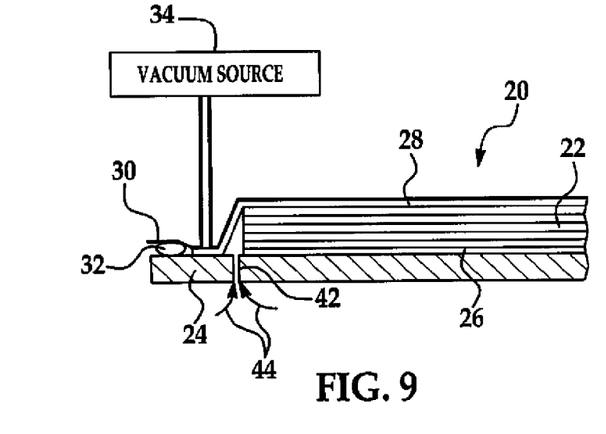
FIG. 9 is an illustration similar to FIG. 1, showing a leak in the tool allowing air to enter the vacuum chamber.
Figure 9A:
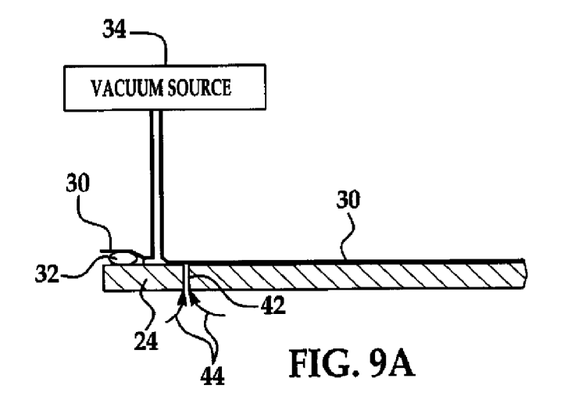
FIG. 9A is an illustration similar to FIG. 9, but showing use of a vacuum bag having colorimetric material to test a tool substrate for air leaks.

The colorimetric material may also be effective in detecting air leaks in other parts of the vacuum bag assembly 20 that cause an undesirable increase of air pressure within the bag 30. For example, as shown in FIG. 9, an air leak 42 may occur in the tool 24 which allows air 44 to enter the vacuum chamber formed over the layup 22. In accordance with the disclosed embodiments, the oxygen contained the air flowing in through the leak 42 is sensed by the layer of colorimetric material 36 on the inner face 30a (FIG. 7) of the bag 30. As previously described, the colorimetric material 36 reacts to the oxygen introduced through the leak 42 by changing its color display, and this change in localized color display may be visually seen through the transparent bag 30 by an operator without the aid of specialized equipment. As illustrated by this example, the colorimetric material 36 may be used to detect air leaks in a variety of underlying substrates, including but not limited to tools used in processing composite parts. Thus, as shown in FIG. 9A, the use of the colorimetric material 36 inside the bag 30 may be employed according to the disclosed embodiments to test a tool 24 or other part or substrate for possible leaks before the tool 24 is placed into use in processing parts such as the layup 22. In order to carry out such testing, the bag 20 having an applied layer of the colorimetric material 36 is sealed to the tool 24, but without placing the layup 22 or other part on the tool 26. A vacuum is then drawn within the bag 30, causing the air pressure within the bag 30 to drop, which then allows the atmospheric pressure to push the bag 30 down onto the tool surface 28. After the colorimetric material 36 is activated with UV light 38, an operator may detect leaks 42 in the tool 24 by visually observing any color changes that may occur in the material 36 seen through the transparent bag 50.

It should be noted here that while the use of the colorimetric material 36 to detect air leaks has been described in connection with vacuum bag curing of composite layups, it may also be used in other applications where vacuum bags are employed in industrial processes. For example, the colorimetric material 36 may be used to detect leaks in vacuum bags that are used to apply compaction pressure to two or more parts (not shown) that are being bonded together with an adhesive.

Figure 10:
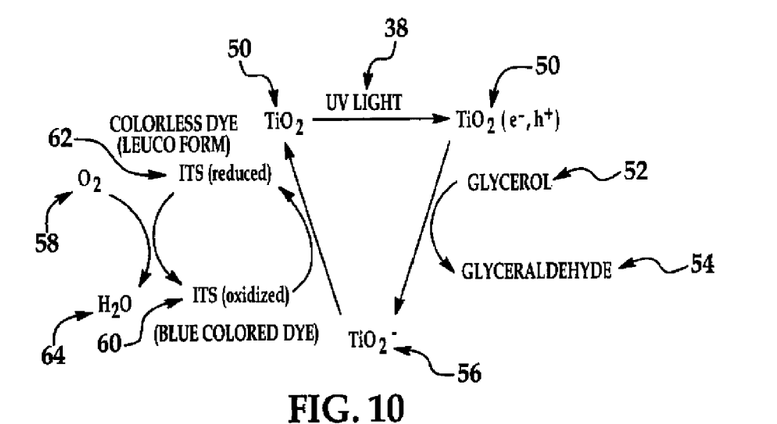
FIG. 10 is an illustration useful in explaining activation of the colorimetric which includes an oxidation-reduction reaction.
Figure 11:
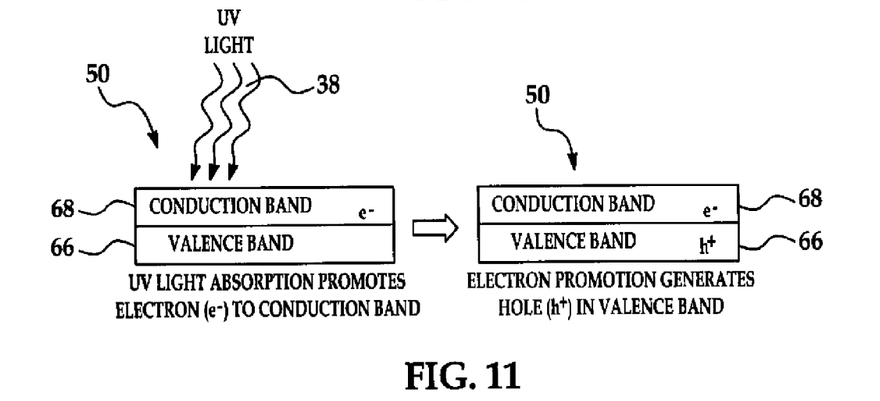
FIG. 11 is an illustration useful in explaining how the absorbsion of UV light by the colorimetric layer of ink creates electron-hole pairs which promote the oxidation-reduction reaction.

Attention is now directed to FIGS. 10 and 11 which diagrammatically illustrate the physical and chemical reactions involved in the activation of the colorimetric material 36 and the related color changes in the redox indicator following activation and subsequent exposure to oxygen as a result of a bag leak. As previously stated, prior to activation, the material 36 may be typically be deeply colored. Irradiation of the ink 36 with UV light 38 (FIG. 9) results in excitation of the $TiO_2$ semiconductor 50 where electron-whole pairs $e^-$, $h^+$ are created.

The absorption of the UV light 38 by the semiconductor 50 results in the promotion of an electron $e^-$ from the valence band 66 (FIG. 10) of the semiconductor 50 to its conduction band 68. When the electron $e^-$ is promoted to the conduction band 68, it also creates an electron hole $h^+$ that contains a positive partial charge. The hole $h^+$ promotes the oxidation of the electron donor, which in the illustrated example is glycerol 52 that is irreversibly oxidized to glyceraldehyde 54. The photo-generated electrons $e^-$ in the semiconductor 50 represented at 56 also reduce the redox indicator, which in the illustrated example is represented by "ITS (reduced)" and designated by the numeral 58. In its reduced or LEUKO form 58, the ITS redox indicator is substantially colorless and remains so in the absence of oxygen. However, when exposed to oxygen, the redox indicator oxidizes back to its colored form represented as "ITS (oxidized)" 60. This redox reaction also converts the $O_2$ to $H_2O$. It should be noted here that the ink 36 can be reused by repeated application of UV light 38 and that a variety of differential color changes and sensitivities are possible.

Figure 12:
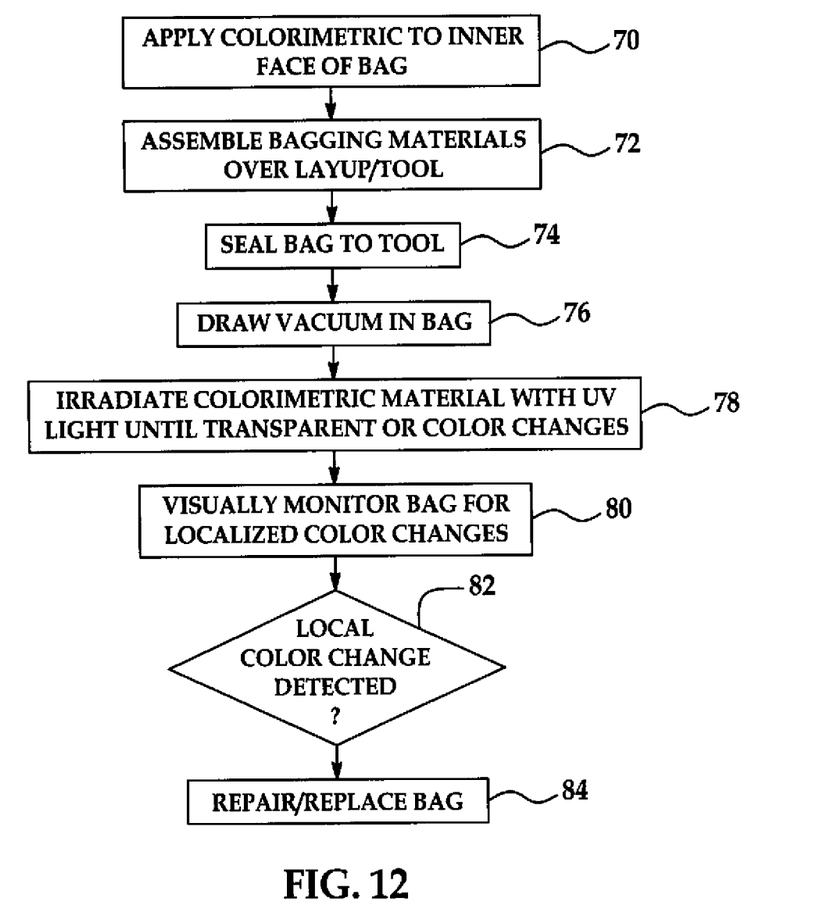
FIG. 12 is an illustration of a flow diagram showing the overall steps of a method of leak detection in vacuum bags.

Attention is now directed to FIG. 12 which illustrates the overall steps of a method of detecting leaks in vacuum bags using human visual observation. Beginning at step 70, a colorimetric material 36 is applied to the inner face 30a of a substantially transparent, flexible bag 30 using any of the application processes previously described. Next, at step 72, the bag assembly 20 is prepared which may include assembling the bagging materials such as a release film 26, part layup 22, breather 28 and bag 30 (FIGS. 1 and 2). At step 74, the bag 30 is sealed to the tool 24, creating a substantially air tight vacuum chamber over the part layup 22 following which, a vacuum is drawn in the bag at 76 at step 78 which evacuates the bag of air.

At step 78, the bag is irradiated with UV light which passes through the transparent bag onto the colorimetric ink 38. The colorimetric ink 38 is irradiated with the UV light until the ink 36 changes color or becomes substantially colorless or transparent, thereby activating the material 36 as an oxygen sensor. At step 80, an operator visually monitors the bag for localized appearances of color or changes in color indicative of a possible leak. At step 82, local appearances of color or changes in color in the bag may be detected by the operator indicating the presence of an air leak in the bag. Upon detection of an air leak, an operator may repair or replace the bag, as shown at step 84.

Figure 13:
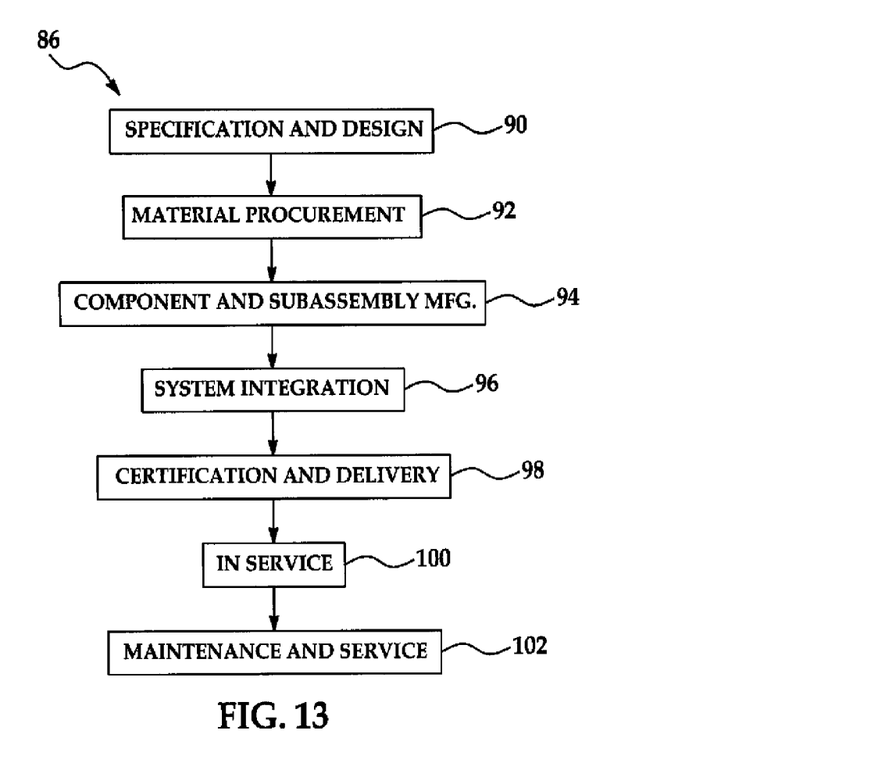
FIG. 13 is an illustration of a flow diagram of aircraft production and service methodology.
Figure 14:
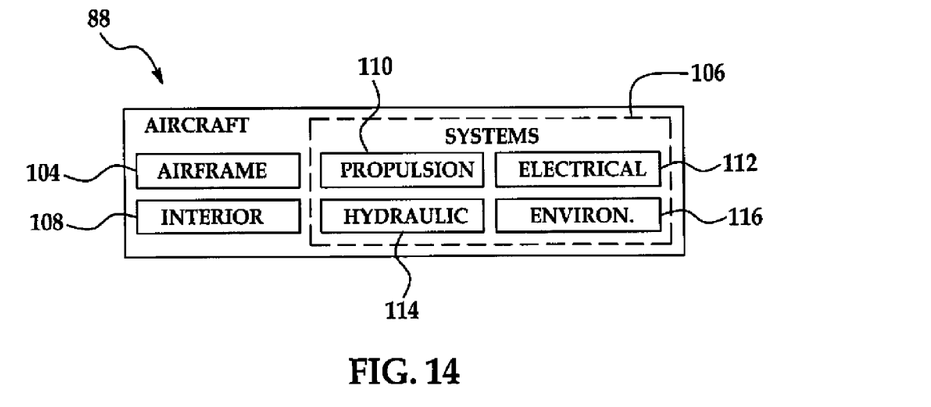
FIG. 14 is an illustration of a block diagram of an aircraft.

Embodiments of the disclosure may find use in a variety of potential applications, particularly in the transportation industry, including for example, aerospace, marine and automotive applications. Thus, referring now to FIGS. 13 and 14, embodiments of the disclosure may be used in the context of an aircraft manufacturing and service method 86 as shown in FIG. 12 and an aircraft 88 as shown in FIG. 14. Aircraft applications of the disclosed embodiments may include, for example, a wide variety of composite structural components, assemblies and subassemblies. During preproduction, exemplary method 86 may include specification and design 90 of the aircraft 88 and material procurement 92. During production, component and subassembly manufacturing 94 and system integration 96 of the aircraft 88 takes place. Thereafter, the aircraft 88 may go through certification and delivery 98 in order to be placed in service 100. While in service by a customer, the aircraft 88 is scheduled for routine maintenance and service 102 (which may also include modification, reconfiguration, refurbishment, and so on). The disclosed embodiments may be employed to carry repairs requiring bonding of parts during the maintenance and service 102.

Each of the processes of method 110 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 14, the aircraft 88 produced by exemplary method 86 may include an airframe 104 with a plurality of systems 106 and an interior 108. Examples of high-level systems 106 include one or more of a propulsion system 110, an electrical system 112, a hydraulic system 114, and an environmental system 116. Any number of other systems may be included. The disclosed method and device may be employed to fabricate structural components used in the airframe 104 and assemblies or subassemblies used in the interior 108. The embodiments may also be used to bond components forming part of the interior 108 or the airframe 104. Although an aerospace example is shown, the principles of the disclosure may be applied to other industries, such as the marine and automotive industries.

Systems and methods embodied herein may be employed during any one or more of the stages of the production and service method 86. For example, assemblies or subassemblies corresponding to production process 94 may be fabricated or manufactured in a manner similar to components or subassemblies produced while the aircraft 88 is in service. Also, one or more apparatus embodiments, method embodiments, or a combination thereof may be utilized during the production stages 95 and 96, for example, by substantially expediting assembly of or reducing the cost of an aircraft 112. Similarly, one or more of apparatus embodiments, method embodiments, or a combination thereof may be utilized while the aircraft 112 is in service, for example and without limitation, to maintenance and service 102.

Although the embodiments of this disclosure have been described with respect to certain exemplary embodiments, it is to be understood that the specific embodiments are for purposes of illustration and not limitation, as other variations will occur to those of skill in the art.

What is claimed:

1. Apparatus for compacting a composite part, comprising:
   a tool adapted to have the composite part placed thereon;
   a substantially transparent, gas impermeable film forming a bag adapted to be placed over the part and sealed to the tool, the film having an inside face, the bag configured to receive a vacuum applied on the inner face;
   a selectively activatable, colorimetric ink on the inside face of the film for providing a visual indication of the location of any air leaks in the film;
   a vacuum source for drawing the vacuum within the bag; and
   a radiation source for directing radiation through the film onto the colorimetric ink for activating the ink to an oxygen reactive state after the vacuum has been drawn in the bag,
   wherein the selectively activatable, colorimetric ink is configured to transition from a first color to a second color upon activation, and from the second color to a third color due to an oxidation-reduction reaction in areas of the film exposed to oxygen, the colorimetric ink configured to transition to the third color upon air leaking into the bag, and wherein the first color is blue, the second color is colorless, and the third color is green.

2. The apparatus of claim 1, wherein the radiation source emits radiation generally within the ultraviolet band of wavelengths.

3. The apparatus of claim 1, wherein the colorimetric ink includes:
   an oxygen permeable binder,
   semiconductor nanoparticles dispersed in the binder,
   an electron donor material, and
   a reduction-oxidation indicator material.

4. A method of processing a part, comprising:
   providing a material that may be activated from a first state in which the material exhibits a first color, to a second state in which the material has a second color that is substantially colorless but reverts substantially to a third color when exposed to oxygen, wherein the first color is blue and the third color is green;
   applying a layer of the material in its first state on an inner face of an oxygen impermeable film;
   placing the film over the part with the inner face of the film facing the part;
   sealing the film around the part to form a vacuum chamber;
   drawing a vacuum within the vacuum chamber;
   activating the material from the first state to the second state; and
   detecting air leaks in the film by visually observing a localized presence of the third color in the layer of material.

5. The method of claim 4, wherein applying the layer of material is performed by one of:
   printing the material onto the inner face of the film,
   spin casting the material onto the inner face of the film,
   spraying the material onto the inner face of the film, and
   co-extruding the layer of material with the film.

6. The method of claim 4, wherein activating the material is performed after the vacuum has been drawn.

7. The method of claim 4, wherein activating the material is performed by directing UV (ultraviolet) light through the film onto the layer of material until the material becomes substantially colorless.

8. Apparatus for compacting a composite layup, comprising:
   a tool adapted to have the composite layup placed thereon;
   a substantially transparent, gas impermeable film forming a vacuum bag adapted to be placed over the part and sealed to the tool, the film having an inside face, the bag configured to receive a vacuum applied on the inner face;
   a selectively activatable, colorimetric ink on an inside face of the film for providing a visual indication of the location of any air leaks in the bag, the colorimetric ink being activatable from a first oxygen insensitive state in which the ink exhibits a first color, to a second oxygen sensitive state in which the ink has a second color that is colorless but changes to a third color when exposed to oxygen, wherein the first color is blue and the third color is green, the colorimetric ink including—
   an oxygen permeable polymer binder,
   $TiO_2$ nanoparticles dispersed in the polymer binder,
   glycerol functioning as an electron donor material, and
   indigo-tetrasulfonate functioning as a reduction-oxidation indicator;
   a vacuum source for drawing a vacuum within the bag; and
   a UV (ultraviolet) light source for directing radiation through the film onto the colorimetric ink for activating the ink from the first state to the second state after the vacuum has been drawn in the bag.

9. A method of compacting a composite layup, comprising:
   placing the composite layup on a tool;
   forming a vacuum bag using a substantially transparent, gas impermeable film;
   preparing a colorimetric material by mixing hydroxyethyl cellulose, nanoparticles of $TiO_2$, glycerol, and indigo-tetrasulfonate;
   applying a layer of colorimetric material on an inside face of the film, the colorimetric material being activatable from a first oxygen insensitive state in which the material exhibits a first color, to a second oxygen sensitive state in which the ink has a second color that is colorless but reverts to a third color when exposed to oxygen, wherein the first color is blue and the third color is green;
   placing the bag over the layup;
   sealing the bag to the tool to form a substantially gas tight enclosure over the layup;
   generating a vacuum within the sealed bag;

activating the layer of colorimetric material from the first state thereof to the second state by directing UV (ultraviolet) light through the bag onto the layer of colorimetric material; and detecting leaks in the bag by visually observing localized changes in the third color of the colorimetric material.

\* \* \* \* \*